United States Patent
Yamatake

(10) Patent No.: US 7,716,277 B2
(45) Date of Patent: May 11, 2010

(54) IMAGE DATABASE SYSTEM

(76) Inventor: Satoshi Yamatake, 2-59-7 Kikunodai, Chofu-shi, Tokyo 182-0007 (JP)

( * ) Notice: Subject to any disclaimer, the term of this patent is extended or adjusted under 35 U.S.C. 154(b) by 980 days.

(21) Appl. No.: 11/109,830

(22) Filed: Apr. 20, 2005

(65) Prior Publication Data

US 2005/0244082 A1    Nov. 3, 2005

Related U.S. Application Data

(63) Continuation of application No. PCT/JP2004/009003, filed on Jun. 25, 2004.

(30) Foreign Application Priority Data

Jul. 2, 2003    (JP)    ............................ 2003-270403

(51) Int. Cl.
  *G06F 15/16*    (2006.01)
  *G06F 7/00*    (2006.01)
  *G06F 17/30*    (2006.01)
(52) U.S. Cl. .......................... 709/203; 707/2; 707/200; 709/219; 714/18
(58) Field of Classification Search .................... 707/2, 707/200; 709/203, 219, 228, 229; 714/18
See application file for complete search history.

(56) References Cited

U.S. PATENT DOCUMENTS 5,283,897 A    2/1994    Georgiadis et al.

(Continued)

FOREIGN PATENT DOCUMENTS

EP    1308857 A    5/2003

(Continued)

OTHER PUBLICATIONS

Lowe H J et al, "The Image Engine HPCC Project. A Medical Digital Library System Using Agent-Based Technology to Create an Integrated View of the Electronic Medical Record," Proceedings of the Third Forum on Research and Technology Advances in Washington, DC, USA May 13-15, 1996, pp. 45-56, Digital libraries, 1996, Los Alamitos, CA, USA.

(Continued)

*Primary Examiner*—Albert DeCady
*Assistant Examiner*—Jennifer L Norton
(74) *Attorney, Agent, or Firm*—Smith Patent Office

(57) ABSTRACT

It is an object of the present invention to provide a highly reliable image database system capable of accessing image data at high speed regardless of the increase of the image data and capable of controlling the image data as a whole. A storage unit 1, a control unit 2, an image database server 3 and a DICOM gateway 4 are subjected with each other to network connection. The storage unit 1 stores medical image data. The control unit 2 controls the storage unit. The image database server 3 stores key information associated with the image data stored and applies relay processing between an externally connected viewer and the image database server. The DICOM gateway 4 applies relay processing via a DICOM protocol between a plurality of modality devices externally connected with the image database server and the DICOM gateway. A control unit group, an image database server group, and a DICOM gateway group are constituted by providing at least a plurality of control units, a plurality of image database servers and a plurality of DICOM gateways, and a load balancer for executing load distribution control of every group is provided for every group based on header information of a request.

2 Claims, 13 Drawing Sheets

U.S. PATENT DOCUMENTS

| | | | |
|---|---|---|---|
| 5,721,904 | A | 2/1998 | Ito et al. |
| 5,978,844 | A * | 11/1999 | Tsuchiya et al. ............ 709/221 |
| 6,574,742 | B1 * | 6/2003 | Jamroga et al. ............ 713/400 |
| 6,912,061 | B1 * | 6/2005 | Ozaki ........................ 358/1.15 |
| 2001/0027453 | A1 | 10/2001 | Suto |
| 2002/0030853 | A1 | 3/2002 | Kizaki et al. |
| 2002/0057849 | A1 * | 5/2002 | Senda ........................ 382/284 |
| 2002/0087503 | A1 * | 7/2002 | Judd et al. .................... 707/1 |

FOREIGN PATENT DOCUMENTS

| | | | |
|---|---|---|---|
| JP | 62-197858 A | 9/1987 |
| JP | 4-229356 A | 8/1992 |
| JP | 4-246783 A | 9/1992 |
| JP | 6-51915 A | 2/1994 |
| JP | 6-112926 A | 4/1994 |
| JP | 6-175904 A | 6/1994 |
| JP | 6-335456 A | 12/1994 |
| JP | 7-175697 A | 7/1995 |
| JP | 7-262066 A | 10/1995 |
| JP | 7-320034 A | 12/1995 |
| JP | 8-328758 A | 12/1996 |
| JP | 9-269871 A | 10/1997 |
| JP | 10-171769 A | 6/1998 |
| JP | 10-198590 A | 7/1998 |
| JP | 11-239165 A | 8/1999 |
| JP | 11-316786 A | 11/1999 |
| JP | 2000-222503 A | 8/2000 |
| JP | 2000-270325 A | 9/2000 |
| JP | 2001-125995 A | 5/2001 |
| JP | 2001-126007 A | 5/2001 |
| JP | 2001-195202 A | 7/2001 |
| JP | 2001-251596 A | 9/2001 |
| JP | 2001-273364 A | 10/2001 |
| JP | 2001-285597 A | 10/2001 |
| JP | 2001-290883 A | 10/2001 |
| JP | 2001-344141 A | 12/2001 |
| JP | 2002-111987 A | 4/2002 |
| JP | 2002-149621 A | 5/2002 |
| JP | 2002-215336 A | 8/2002 |
| JP | 2002-245173 A | 8/2002 |
| JP | 2003-22209 A | 1/2003 |
| JP | 2003-164442 A | 6/2003 |
| JP | 2003-296451 A | 10/2003 |

OTHER PUBLICATIONS

Stephen T C Wong et al, "A Hospital Integrated Framework for Multimodality Image Base Management", IEEE Transactions on Systems, Man and Cybernetics. Part A: Systems and Humans, Jul. 1, 1996, vol. 26, No. 4, pp. 455-469, IEEE Service Center, Piscataway, NJ, USA.

Sotiris A Pavlopoulos et al, "Designing and Implementing the Transition to a Fully Digital Hospital", IEEE Transactions on Information Technology in Biomedicine, Mar. 1, 1999, vol. 3 No. 1, pp. 6-19, IEEE Service Center, Los Alamitos, CA, USA.

* cited by examiner

| Storage unit ID | Failure flag | Residual capacity | Drive ID | Failure flag | Residual capacity | Control unit ID | Updated date and time |
|---|---|---|---|---|---|---|---|
| 1 | 0 | xxx | 1 | 0 | xxx | 1 | 2003.3.4. 15:30 |
| | | | 2 | 0 | xxx | | |
| | | | 3 | 0 | xxx | | |
| | | | 4 | 0 | xxx | | |
| | | | 5 | 0 | xxx | | |
| 2 | 0 | xxx | 1 | 0 | xxx | 1 | 2003.3.4. 15:35 |
| | | | 2 | 0 | xxx | | |
| | | | 3 | 1 | xxx | | |

FIG.13

IMAGE DATABASE SYSTEM

CROSS REFERENCE TO RELATED APPLICATIONS

This application is a continuation application of International Application No. PCT/JP2004/009003 filed on Jun. 25, 2004, currently pending which claims priority to Japanese Patent Application No. 2003-270403 filed on Jul. 2, 2003. The disclosure of International Application No. PCT/JP2004/009003 and Japanese Patent Application No. 2003-270403 are hereby incorporated by reference.

BACKGROUND OF THE INVENTION

1. Field of the Invention

The present invention relates to an image database system for storing a large quantity of medical image information photographed by a modality device such as a CT device and an MRI device as electronic information and for being useful for diagnosis.

2. Description of the Related Art

Japanese Patent Application Laid-Open (JP-A) No. 2002-245173discloses a medical image control system which subjects a plurality of image servers for storing medical image generated in a plurality of modality devices to network connection and controls a large quantity of medical images stored in the plurality of image servers. The medical image control system can detect and display a desired medical image at high speed from a plurality of medical image storage servers connected to the network. The medical image control system comprises an integrated control server containing detection means, data base means and control means. The detection means detects a first retrieval information concerning the medical image stored in a plurality of image servers regularly at prescribed time intervals. The data base means adds information concerning the image server to the first retrieval information detected by the detection means when the first retrieval information detected does not exist in a second retrieval information which has been already registered, and registers the information as the second retrieval information. The control means controls a large quantity of medical images stored in the plurality of image servers on the network based on the second retrieval information registered in the data base means. The medical image control system can rapidly access to a desired image server through the integrated control server.

For example, this type of the network is explained by using an OSI (Open Systems Interconnection) reference standard model. A physical layer and data link layer of the network are constituted by Ethernet (registered trade name), and a transport layer and a network layer are constituted by TCP/IP (Transmission Control Protocol/Internet Protocol). High order layers of a session layer or more are constituted by a DICOM (Digital Imaging and Communication for Medicine) protocol which is an image diagnostic standard in a medical field. The medical images are stored and controlled as a DICOM image comprising tag information and image data in each image server (DICOM server) through the network, and are interpreted and browsed by using an image viewer (DICOM viewer) for exclusive use.

However, according to the DICOM protocol in the conventional image database system as described above, the image data is essentially treated in a non-compression state. In addition, a communication procedure is complicated from the viewpoint of the protection of the tag information or the like, and it takes a time for data communication. Thereby, it is necessary to improve an image search response or the like. In particular, a lot of viewers are also set in a large-scale hospital, and the increase of network load causes the additional reduction of response.

In the above system, a large quantity of medical image data is respectively controlled by a plurality of different image servers for every modality device. The medical image data is backed up by a different system in a different media for every image server which is manufactured by a different manufacturer and is different model. Thereby, a problem exists in the control of the image data as a whole system is inadequate.

The image viewer connected to the above network may be set in an operating room, and may be used as an assistance of an operation. A request exists in that the reliability of the image viewer must be fully guaranteed.

SUMMARY OF THE INVENTION

The present invention has been accomplished in view of the foregoing and other problems in prior art. Accordingly, it is an object of the present invention to provide a highly reliable image database system capable of accessing the image data at high speed to the apparatus using the DICOM protocol regardless of the increase of the image data, and capable of controlling the image data as total.

An image database system according to the present invention so as to attain the object, comprising:

a storage unit for storing medical image data;

a control unit for controlling the storage unit;

an image database server for storing attribute information including key information associated with the medical image data stored in the storage unit and for applying relay processing of the medical image data between an externally connected apparatus and the image database server;

a DICOM gateway for applying relay processing of the medical image data via a DICOM protocol between a plurality of modality devices externally connected with the image database server and the DICOM gateway; and a switch for subjecting the storage unit, the control unit, the image database server and the DICOM gateway with each other to network connection, wherein a control unit group, an image database server group, and a DICOM gateway group are constituted by providing at least a plurality of control units, a plurality of image database servers and a plurality of DICOM gateways, and a load balancer for executing load distribution control of every group is provided based on header information of a request.

Further, an image database system according to the present invention, comprising:

a storage unit for storing medical image data;

a control unit for controlling the storage unit;

an image database server for storing attribute information including key information associated with the medical image data stored in the storage unit and for applying relay processing of the medical image data between an externally connected apparatus and the image database server, a DICOM gateway for applying relay processing of the medical image data via a DICOM protocol between a plurality of modality devices externally connected with the image database server and the DICOM gateway; and a switch for subjecting the storage unit, the control unit, the image database server and the DICOM gateway with each other to network connection, wherein a control unit group, an image database server group, and a DICOM gateway group are constituted by providing at least a plurality of control units, a plurality of image database servers and a plurality of DICOM gateways, and a load balancer for executing load distribution control of every group is provided based on header information of a request, and wherein the control unit, the image database server and the DICOM gateway are subjected with each other to the network connection by a first network through a first switch for processing a job related to an external request from a viewer or the modality device, and a second network through a second switch for processing a job related to an internal request.

Further, another invention will be apparently shown by referring to the following embodiments.

BRIEF DESCRIPTION OF THE DRAWINGS

FIG. 13 is an illustration of a table showing an operating state.

DESCRIPTION OF THE PREFERRED EMBODIMENTS

Figure 1:
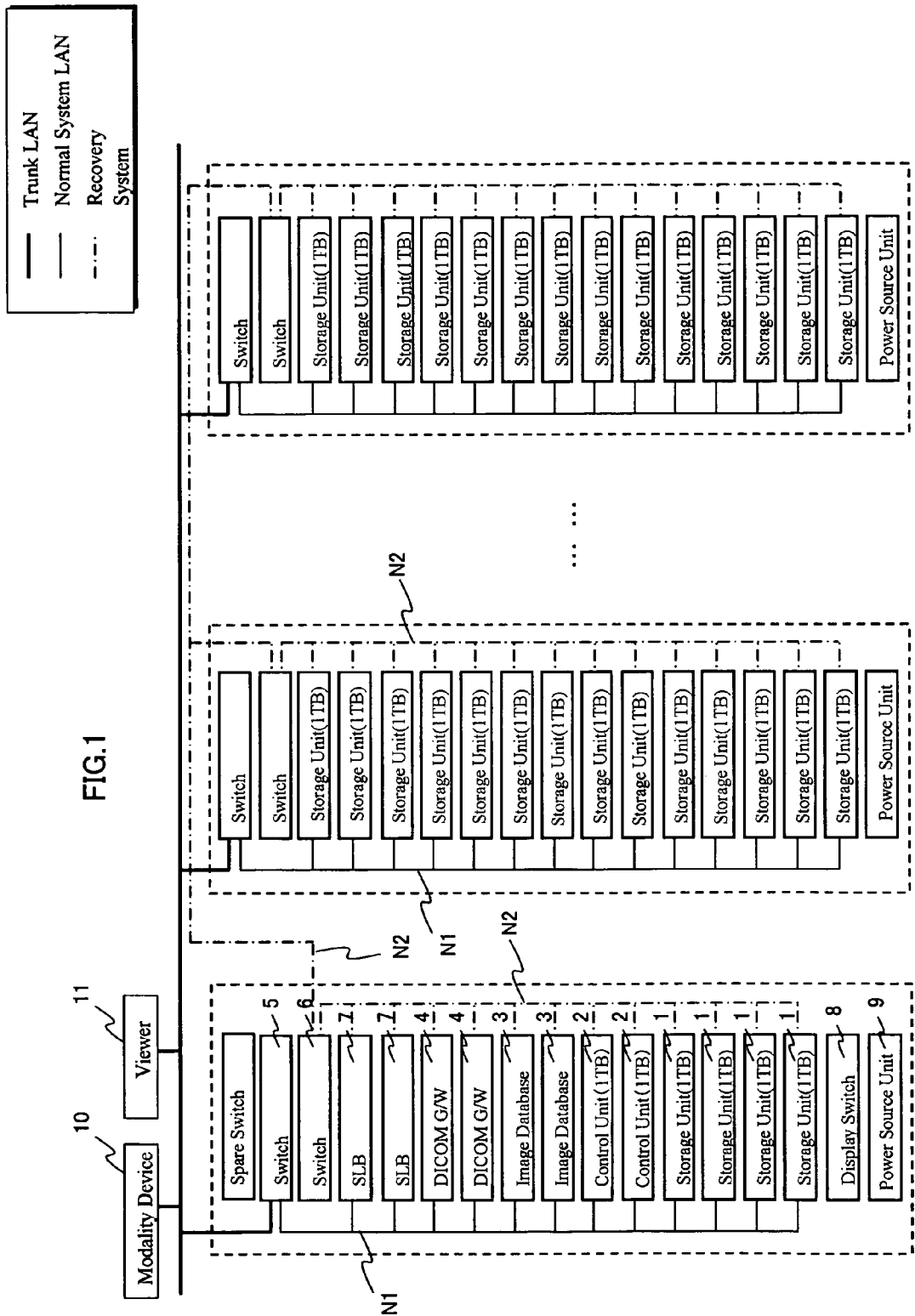
FIG. 1 is a constitution diagram of an image database system according to the present invention.

Referring to the drawings, the image database system according to the present invention will be described below.

As shown in FIG. 1, the image database system comprises a basic frame (basic minimum tower) and a plurality of extended frames (expanded tower).

The basic frame is constituted by subjecting a storage unit group, a control unit group, an image database server group and a DICOM gateway group with each other to network connection through switches 5 and 6. The storage unit group contains four storage units 1 for storing medical image data. The control unit group contains two control units 2 for controlling each storage unit 1. The image database server group contains two image database servers 3 for storing attribute information including key information associated with the medical image data stored in each storage unit 1 and for applying relay processing of the medical image data between an externally connected viewer 11 and the image database server. The DICOM gateway group contains two DICOM gateways 4 for applying relay processing of the medical image data via a DICOM protocol between a plurality of modality devices 10 externally connected to the image database server 3 and the DICOM gateways. Two load balancers 7 for executing load distribution control of every group is provided for every group based on header information of a request through the network, and a display switch 8 and a power source unit 9 are provided. Herein, the number of units or servers should be a mere exemplar, and the invention is not limited thereto.

The extended frame comprises a power source unit, a plurality of storage units and switches. The extended frame can be extended so that image data with a high capacity can be stored.

The storage units 1, the control units 2, the image database servers 3 and the DICOM gateways 4 are subjected with each other to network connection by a first network N1 through a first switch 5 for processing a job related to an external request from the viewer 11 or the modality device 10, and a second network N2 through a second switch 6 for processing a job related to an internal request. In the networks N1 and N2, a physical layer and data link layer of the network are constituted by Ethernet (registered trademark) of 1000 BASE-T in an OSI reference standard model, and a transport layer and a network layer are constituted by a TCP/IP. High order layers of a session layer or more are operated by a DICOM protocol which is an image diagnostic standard in a medical field, or another local high order protocol.

Two load balancers 7 are connected to each other by a local communication line (RS232-C), and one load balancer is usually operated. For example, load distribution control is executed so that the load of each component may become equivalent by a round-robin system if there is no difference in the performance of the component of each group, a weighted round-robin system if there is a difference in the performance, and a response time algorithm or the like. When a failure is detected through the local communication line, a spare load balancer is operated. Herein, it is also possible to adopt the communication line by another telecommunication standard other than RS232-C as the local communication line. In addition, the local communication may be performed through the first or the second network.

An apparatus using the DICOM protocol through the DICOM gateway can be connected to the network by the above constitution, and the apparatus such as the viewer due to a non-DICOM protocol can be also connected. Thereby, the flexibility of the system can be secured. In addition, a plurality of control units, a plurality of image database servers and a plurality of DICOM gateways are provided according to the increase in network load, and the load is distributed by the load balancer. Thereby, the stable throughput can be always secured. Since each group is constituted so as to have redundancy in the horizontal direction, each group can cope flexibly without causing system down just in case of a failure, and the reliability can be remarkably improved.

The processing to external requests, such as storage processing of the image data from the modality device through the first network and request processing of the image data from the viewer, and internal processing such as the mutual maintenance of each group through the second network are divided, and can be processed respectively and independently. Thereby, the stability and safety of the system can be improved without causing a decrease in the throughput to the external request.

The operation of the system will be explained below by using the response operation or the like to the image storage request, the image read request from the modality device, and the image inspection request from the viewer as an example.

The modality device 10 transfers the image storage request via the DICOM protocol at a virtual IP address (VIP) assigned to the group constituted by two DICOM gateways 4, and starts an association. The load balancer 7 operates normally, and selects the DICOM gateway 4 having the least load. The load balancer 7 intercepts a packet having the virtual IP address as a destination address, and rewrites it to the real IP address of the DICOM gateway 4 selected. The image storage request is received by the selected DICOM gateway 4 according to the above process. The communication of returning packet is established by operating reversely. Herein, the load of the DICOM gateway 4 is distributed in one association by the load balancer 7.

It is excellent in respect of processing efficiency and control efficiency that a series of inspection image data are collectively loaded or saved at the time of the load distribution. Therefore, it is preferable that the load of the DICOM gateway is distributed by making from establishment of the association due to the DICOM protocol to the end in one unit.

Figure 2:
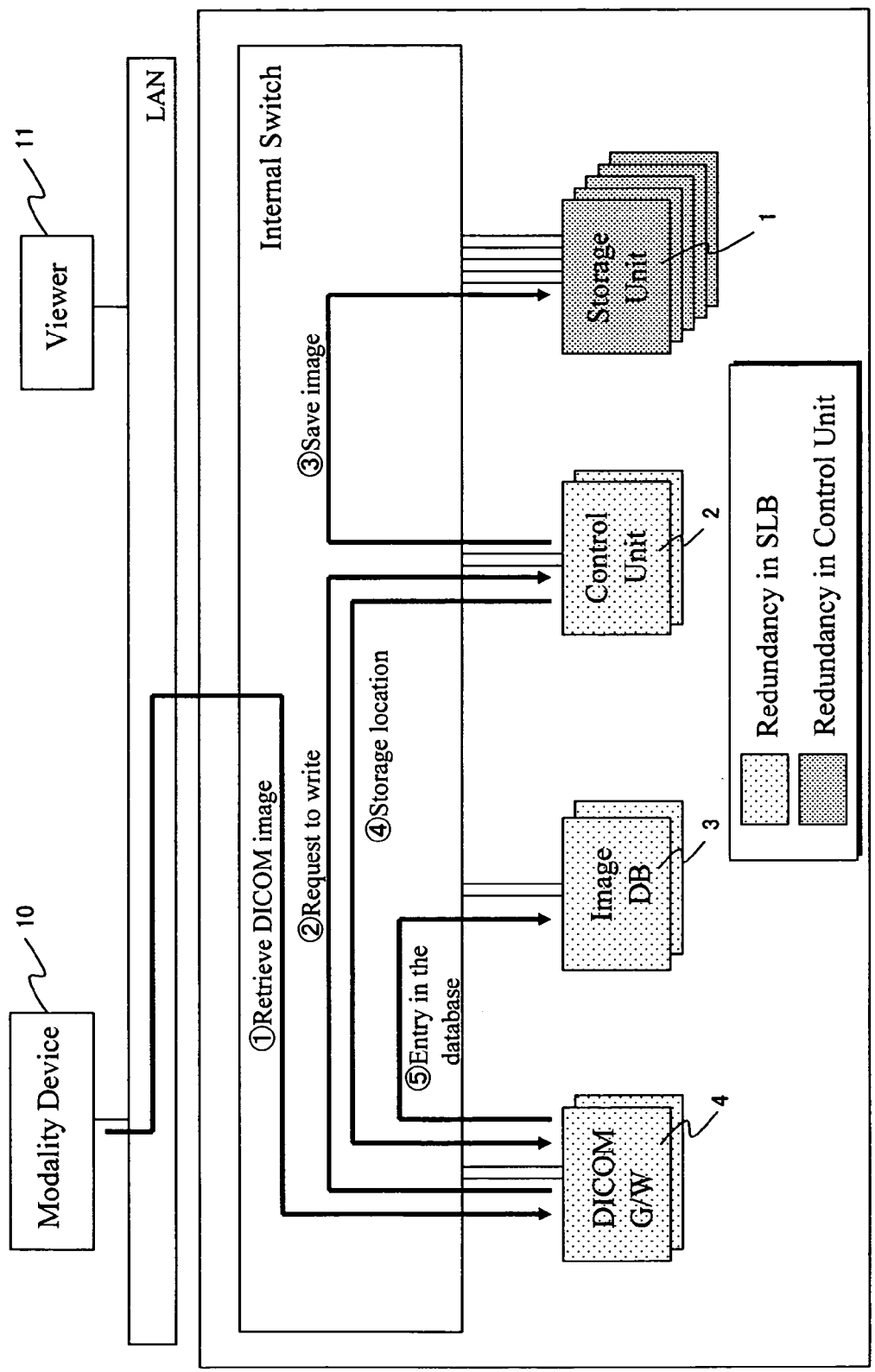
FIG. 2 is an illustration of a procedure for storing images in the image database system according to the present invention.
Figure 3:
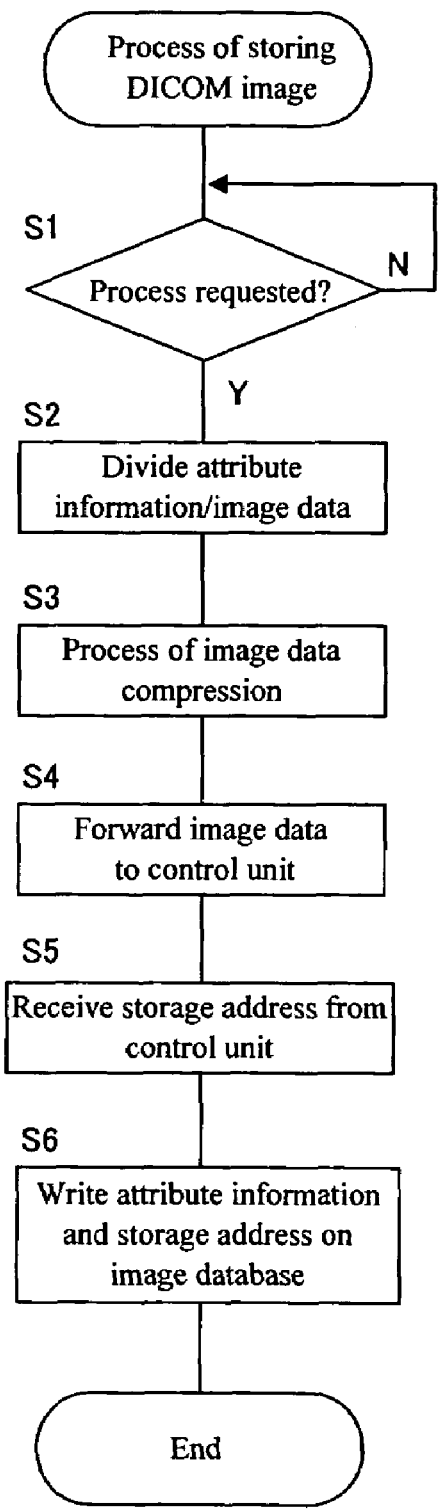
FIG. 3 is a flow chart showing the procedure for storing the images in the image database system according to the present invention.

As shown in FIGS. 2 and 3, the DICOM gateway 4 requested divides the received image information into the attribute information and image information containing an inspection example UID, the name of a patient, a patient ID, an acceptance number, inspection date, inspection time, and the date of birth of a patient. The inspection example UID consists of a distribution source fronting code, a product specific number and a serial number or the like. The divided image data are compressed into a plurality of images each of having different compression ratios by the DICOM gateway 4 and reversible compression process at a predetermined algorithm is given to each of those images. The compressed images are transferred to the control unit 2. Herein, though four kinds of images (an original image having 512×512 pixels, a ¼ image having 256×256 pixels, a ⅟₁₆ image having 128×128 pixels, and a ⅟₆₄ image having 64×64 pixels used as a thumbnail) are generated and stored, the compressed images are not limited thereto. Though PNG (Portable Network Graphics) is used, the other reversible compression algorithm may be used.

The control unit 2 receives the image data transferred. The control unit 2 stores the image data with the algorithm to be described below, and replies the storage address to the DICOM gateway 4. The DICOM gateway 4 transfers the attribute information and the storage address of the image data replied from the control unit 2 to the image database server 3, and directs the update processing of data.

The image data is compressed to a plurality of compressed images having different compression ratios by a predetermined reversible compression algorithm, and thereby the capacity of the image data transferred through the network can be changed according to the required quality. In addition, since the image data is reversibly compressed, the quality of the data after decompression is not degraded. The address in which the image data is stored is saved as table data with the attribute information in the image database server so as to be able to link with the image data.

The control unit 2 and the image database server 3 involved in the above operation are communicated through the first network N1 in the same manner as the DICOM gateway 4, and the load is distributed by the load balancer 7. Though the load of each operation to be explained below is fundamentally distributed by the load balancer 7 as described above, the explanation of the operation of the load balancer is omitted afterward.

Figure 4:
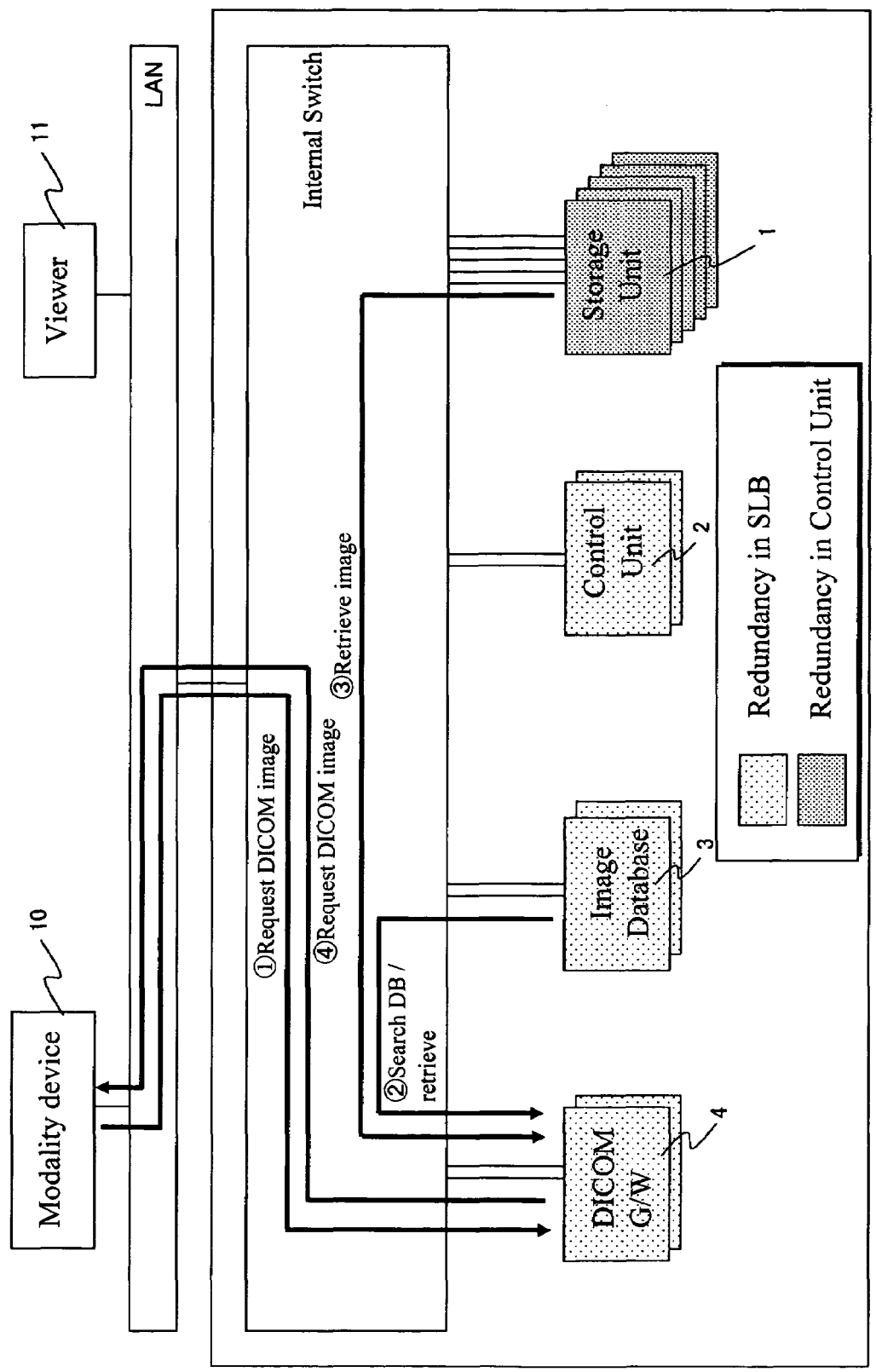
FIG. 4 is an illustration of a procedure for providing images in the image database system according to the present invention.
Figure 5:
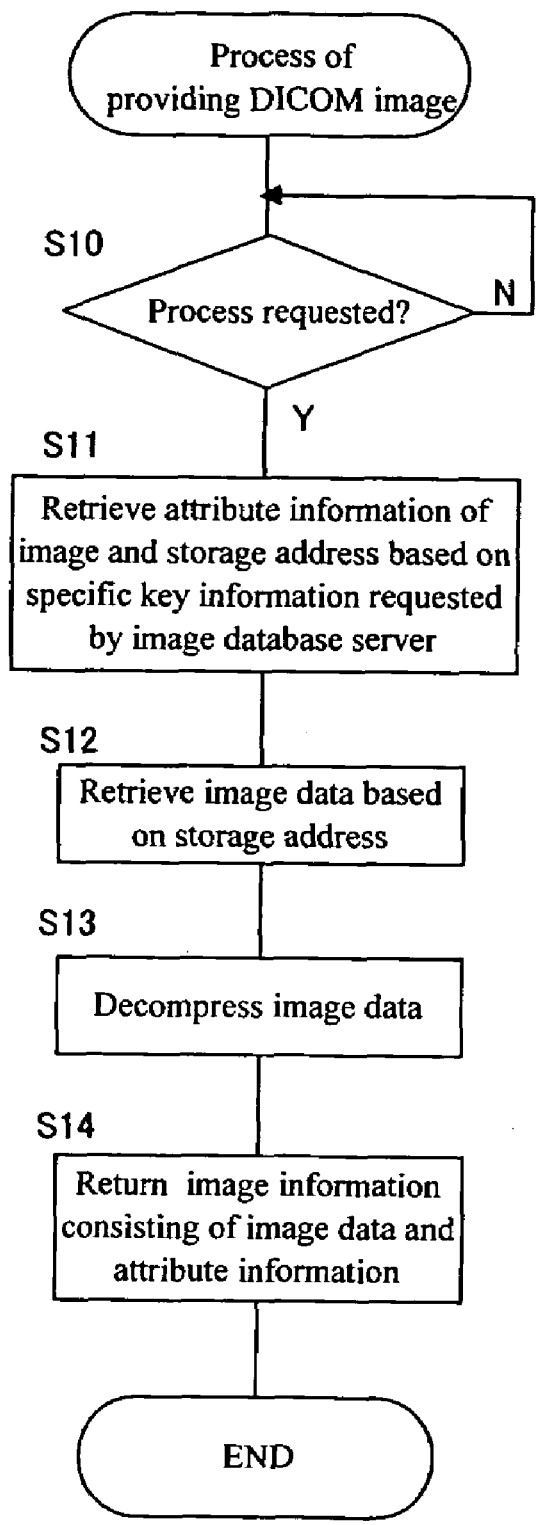
FIG. 5 is a flow chart showing the procedure for providing the images in the image database system according to the present invention.

Next, when the DICOM gateway 4 receives an image providing request from the modality device 10, as shown in FIGS. 4 and 5, the DICOM gateway 4 retrieves the attribute information and the storage address from the image database server 3 based on any key information of the attribute information specifying a request image. The DICOM gateway 4 retrieves the compressed image reversibly compressed from the storage unit 1 based on the storage address, decompresses the compressed image, and replies with the attribute information to the modality device 10 via the DICOM protocol.

Figure 6:
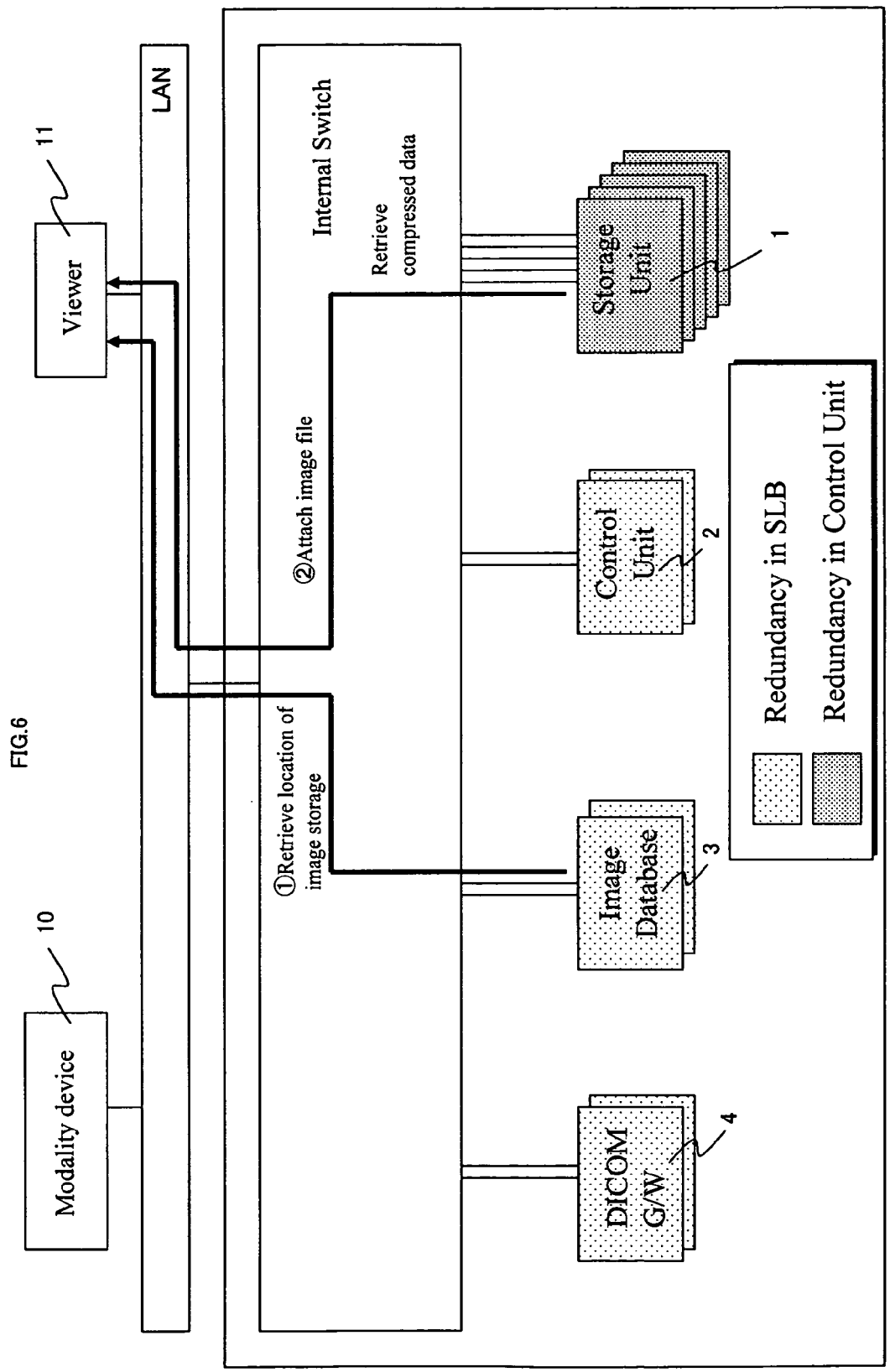
FIG. 6 is an illustration of a procedure for searching images due to a viewer connected to the image database system according to the present invention.
Figure 7:
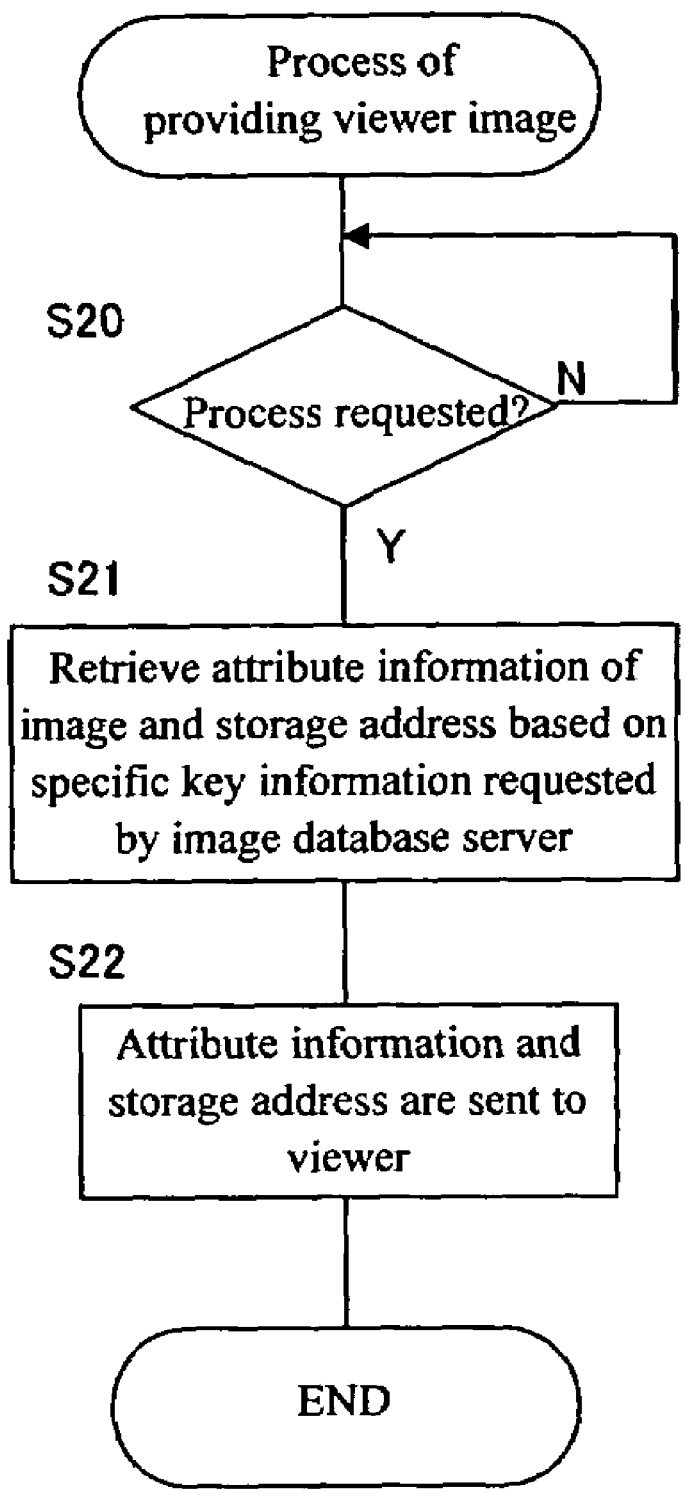
FIG. 7 is a flow chart showing the procedure for searching the images by the viewer connected to the image database system according to the present invention.

As shown in FIGS. 6 and 7, the DICOM gateway 4 retrieves the attribute information and the storage address from the image database server 3 based on any key information of the attribute information specifying the requested image according to the inspection request of the image data from the viewer 11 to the image database server 3, and replies to the viewer 11. Then, the viewer 11 accesses the storage unit 1 based on the storage address received, and retrieves a desired image data. Herein, if the viewer 11 is the DICOM viewer, the viewer 11 is operated through the above DICOM gateway 4. However, if the DICOM protocol is not used, and the local protocol by TCP/IP is supported, any high order protocol can be used.

The control unit 2 is provided with operating state inspection means and failure diagnosis means. The operating state inspection means performs an operating state inspection in order through the second network N2 to each storage unit 1 without through the load balancer 7 when a power source is turned on (The load of the external access to the control unit 2 is distributed by the load balancer 7.). Then, the operating state inspection means updates and stores the result in the table showing the operating state of the image database server 3. The failure diagnosis means performs a failure diagnosis of the other control unit based on the update history of the table showing the operating state data due to the other control unit 2.

Thereby, since the failure situation of a drive in the storage unit or the unit can be grasped, and the latest situations are stored as the table data in the image database server, the effective storage location of the image data can be certainly judged. Whether the other storage units are normally operated or not, can be judged by the update history stored in the table data, and the detection of failure and restoration can be rapidly performed between the control units without providing the other failure detection algorithm.

To be detailed below, the operating state inspection means check and see the attachment status of a storage unit in order in a frame unit, whether the unit is removed or attached, in the storage unit 1 which consists of several hard disks and is loaded on the frame, and in a case which the unit is attached, the disk residual capacity for every drive and the total residual capacity of the unit are given. In addition, the operating state inspection means performs the writing and reading of any file to each drive, and investigates the disk obstacle of each drive. The operating state inspection means updates and stores the result at the table showing the operating state of the database server 3 shown in FIG. 13. Though not apparently written in FIG. 13, the data can be controlled in the frame unit by adding a frame ID to the high order data of the storage unit ID.

The control unit 2 is provided with redundancy storing means for selecting data storage locations of the number of redundancy from the storage units which are identified based on the table showing the operating state and are normally operated to the data storage request to the storage unit 1, and for and storing the data.

To be detailed below, the redundancy storing means investigates the disk residual capacity per drive based on the table showing the operating state, selects the drives of the number of redundancy in which the disk residual capacity is large to a different storage unit, and stores. Herein, the number of redundancy is set to 2. Therefore, the same data will certainly exist in the different storage unit 1 within the system. (Herein, it is needless to say that the number of redundancy may be set to 2 or more.) That is, since a large quantity of image data are backed up under the similar environment whenever a large quantity of image data are generated, it is unnecessary to back up by using the other media, and the image data can be always accessed from the network.

Another method can investigate the disk residual capacity per the storage unit 1, and select two storage units 1 in which the disk residual capacity is large. In addition, the method can select a drive in which the disk residual capacity is large from the storage units 1 selected, and stores the data. The storage address of the data is replied to the transferring origin of a storage request. A reply to the storage request of the above image data is sent to the DICOM gateway 4, and is stored in the database server 3 with the attribute information of the image data or as the attribute information by the DICOM gateway 4.

According to another method, the redundancy storing means may select a plurality of storage units 1 having the residual capacity of a predetermined capacity or more as a candidate based on the table showing the operating state, and select two storage units 1 as an object based on a random number generated by random number generation means. For example, the storage unit of more number than the number of redundancy is selected as the candidate, and any random number of 1 to 9 is generated in order by the random number generation means generates to assign the random number to the storage unit of each candidate. The storage units of the number of redundancy can be selected from the one having a large value of the generated random number. In this case, the load concentrating on the newly added storage unit can be prevented.

Further, according to another method, the redundancy storing means may perform redundancy storage processing by using any method described above to the storage unit mounted on a different frame based on the table showing the operating state. In this case, the influence caused by disasters such as fire, earthquake and flood can be suppressed by setting each frame in a different place and building.

When the redundancy storing means investigates the disk residual capacity based on the table showing the operating state, one having larger residual capacity than the maximum capacity assumed in the image data stored is searched. Conversely, when the residual capacity is smaller than this value, the data indicating the filled drive is stored in the residual capacity data of the table showing the operating state. When all drives of the storage unit 1 are full, the time for investigating the disk residual capacity can be shortened by excluding the storage unit 1 from the object for selection.

Further, when the storage unit 1 or a drive judged to be unusual by the operating state inspection means exists, the control unit 2 retrieves the data storage address of the other storage unit in which the same data as the data stored in the storage unit or a drive judged to be unusual is stored based on the storage address stored in the database server 3 so as to restore the data. The data stored in the data storage address is selected and reproduced from the storage units 1 which is identified based on the table showing the operating state and is normally operated except the storage unit 1 in which the same data is stored. Thus, even if any storage unit breaks down, or is removed, the table showing the operating state to the added storage unit is automatically generated when the image data is automatically reproduced and a new storage unit is added. Thereby, maintenance operation such as the addition and removal of the storage unit can be performed without causing the system down of the power source.

The failure diagnosis means of the control unit 2 accesses the table showing the operating state periodically or irregularly. The failure diagnosis means of the control unit 2 recognizes the failure of the other control unit when the update history does not exist in between the time of access and the past predetermined time based on the update history of the table showing the operating state data due to the other control units 2. The failure diagnosis means of the control unit 2 starts one spare control unit when the spare control unit is equipped.

Herein, the operating state inspection means may be operated by any one of the two control units under operation, and the failure diagnosis means may be operated by the other control unit. In this case, the flag and operation time data showing the completion of the operation of the failure diagnosis means due to the other control unit are recorded on the table showing the operating state, and one control unit checks the flag and the operation time data. Thereby, the failure of the other control unit can be also detected.

The control unit 2 may be constituted integrally with the storage unit 1 on the same substrate. In this case, for example, two storage units are set to an operation state. When one failure is discovered by the failure diagnosis means, the spare control unit can be switched to the operation state.

The update process and failure recovery process of the image database server 3 will be explained below. The image database server 3 is provided with the updating means for updating the database of the image database server 3 to the update processing of data performed through the first network N1 and for updating the database of the other image database server 3 through the second network N2.

The image database server 3 is provided with a port for updating and a port for retrieving to the load balancers 7. Both ports are opened at the normal time. Further, the updating means of one image database server 3 (DB1 in Figure) controls the last operation time of the updating means of the other image database server 3 (DB2 in Figure), and writes in and controls the time of last update on all the records of all tables.

Figure 8:
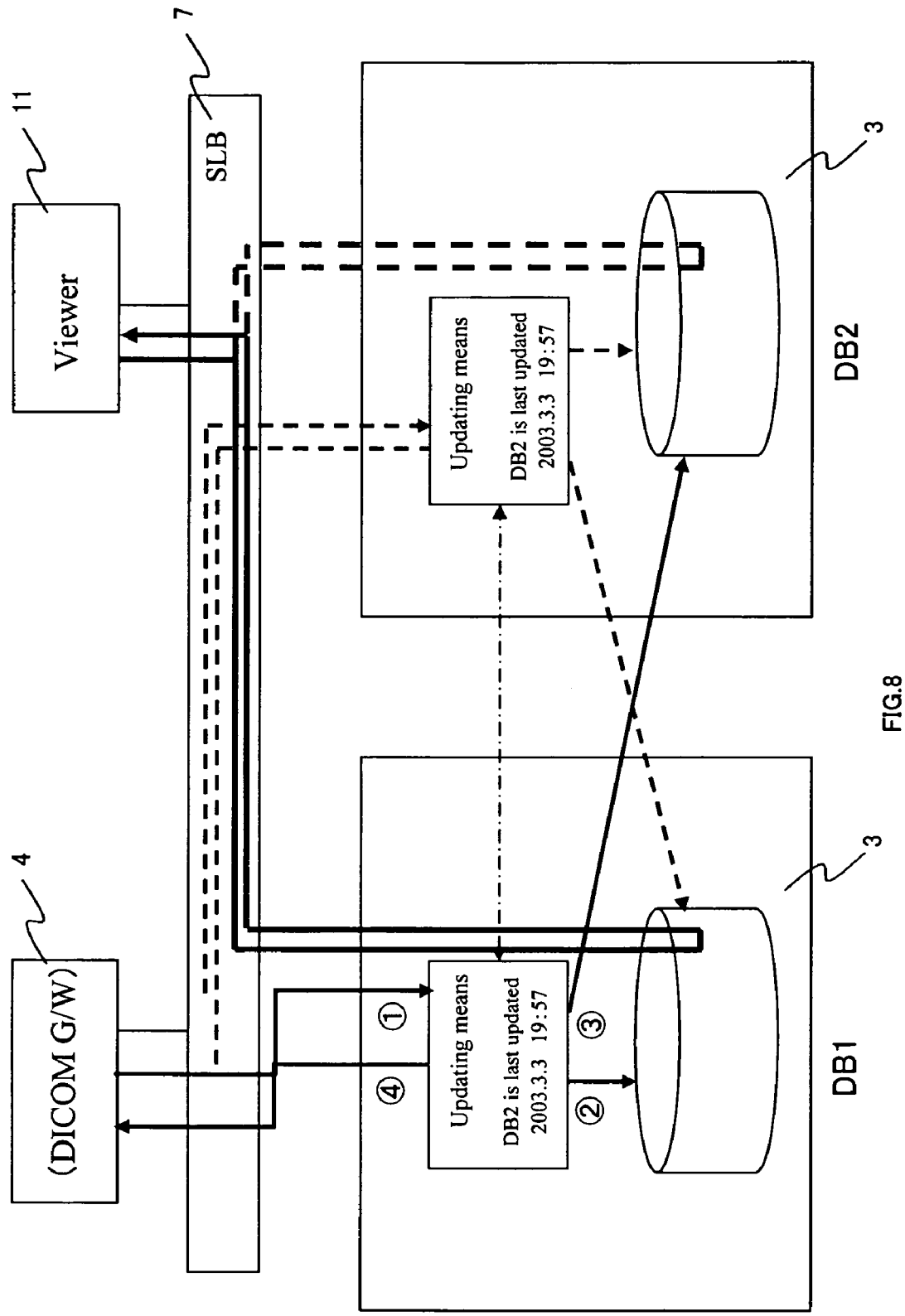
FIG. 8 is an illustration of a data update process by an image database server.
Figure 9:
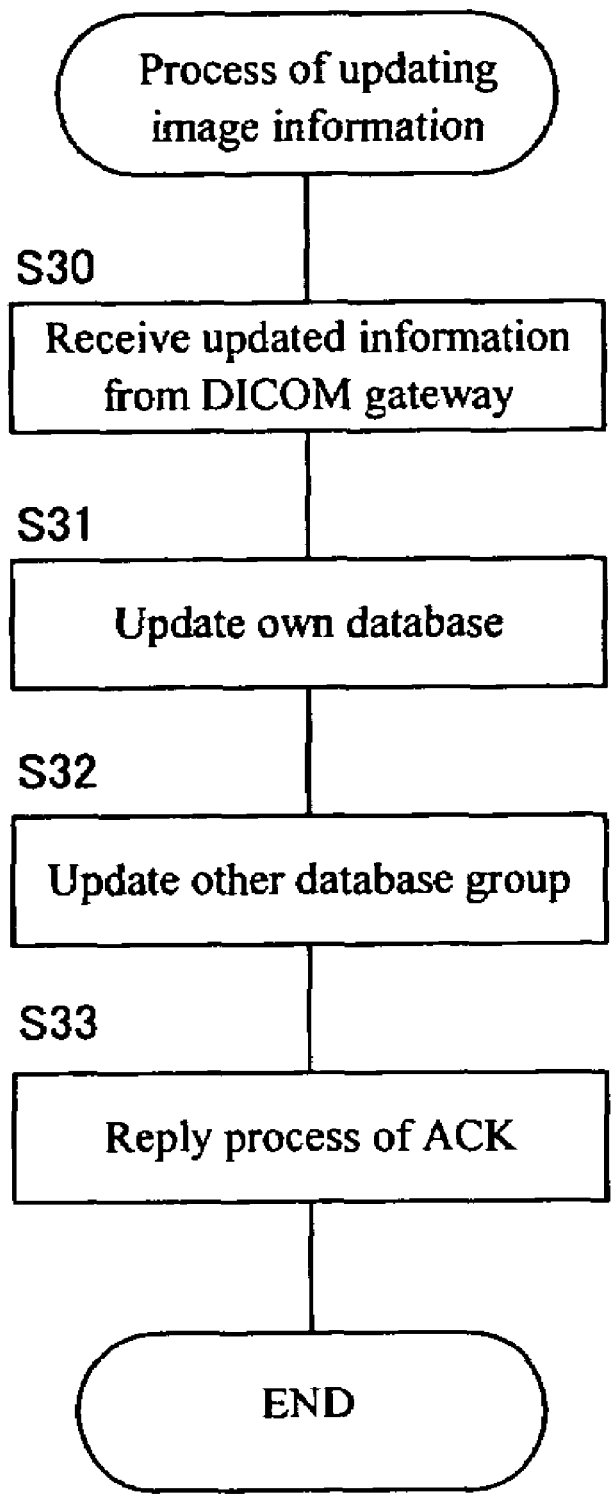
FIG. 9 is a flow chart showing the data update process by the image database server.

As shown in FIGS. 8 and 9, the updating means updates the database (step 2 shown in FIG. 8) according to the data update request such as the storage request of the attribute information of the image data and the storage address of the image data from the DICOM gateway 4 through the load balancer 7, and the storage request of the table showing the operating state from the control unit 2, (step 1 shown in FIG. 8). Then, the updating means updates the database of the other image database server 3 through the second network 2 (step 3 shown in FIG. 8). When this operation is completed, an acknowledgement to the request is sent (step 4 shown in FIG. 8).

As described above, the image database server group comprises a plurality of image database servers, and the load of the image database servers is distributed by the load balancer. Therefore, the table data or the like consisting of the attribute information and storage address of the image data updated by the own controlled data base, i.e., the DICOM gateway described above must be controlled so that the contents always agree with the other image database server. Consequently, the redundancy can be always secured by updating through the second network using the updating means.

The image database server is provided with a port for updating data, and a port for retrieving data to the first network N1. A recovery process means for closing the port for updating data at the time of the recovery processing to the database of the other image database server through the second network N2 is provided.

That is, since the database of the image database server is also updated according to the update request from the DICOM gateway when self-restoring the database of the other database server through the second network at the time of restoring the other database server, the update information is also the restoration object of the other database server, and the recovery process may not be easily advanced. Consequently, the port for updating data is closed to refuse the update of own database, and the recovery process is rapidly performed. In this case, a response to the request to read the image data can be obtained by opening the port for retrieving data.

Figure 10:
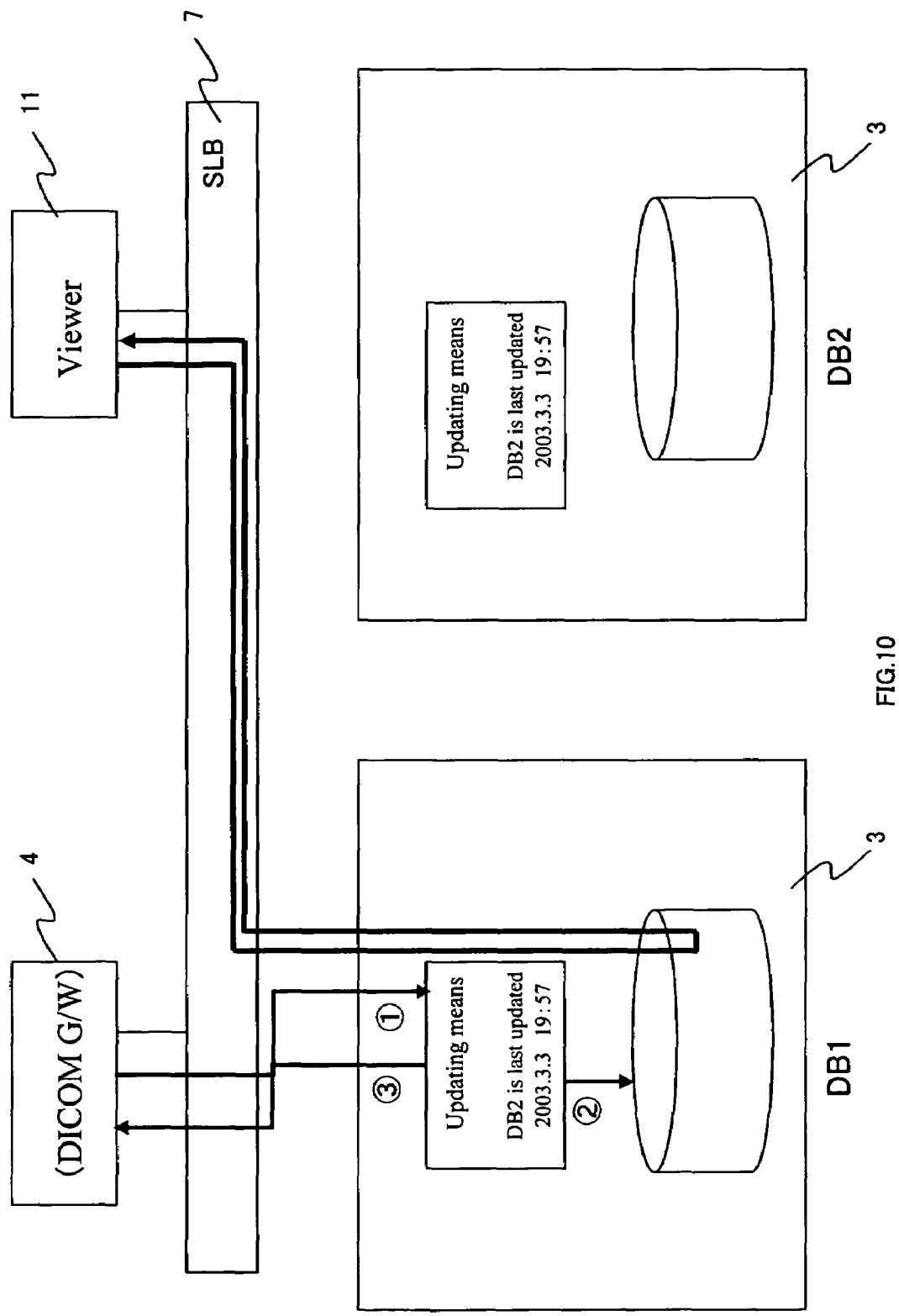
FIG. 10 is an illustration of the data update process by the image database server.

To be detailed below, when the other image database server 3 is out of order, both the port for updating data and the port for retrieving data are closed, and the load balancer 7 requires processing to one of the image database server 3 only. As shown in FIG. 10, in this case, only the update process of own database is performed to the update request, and an acknowledgement is sent.

Figure 11:
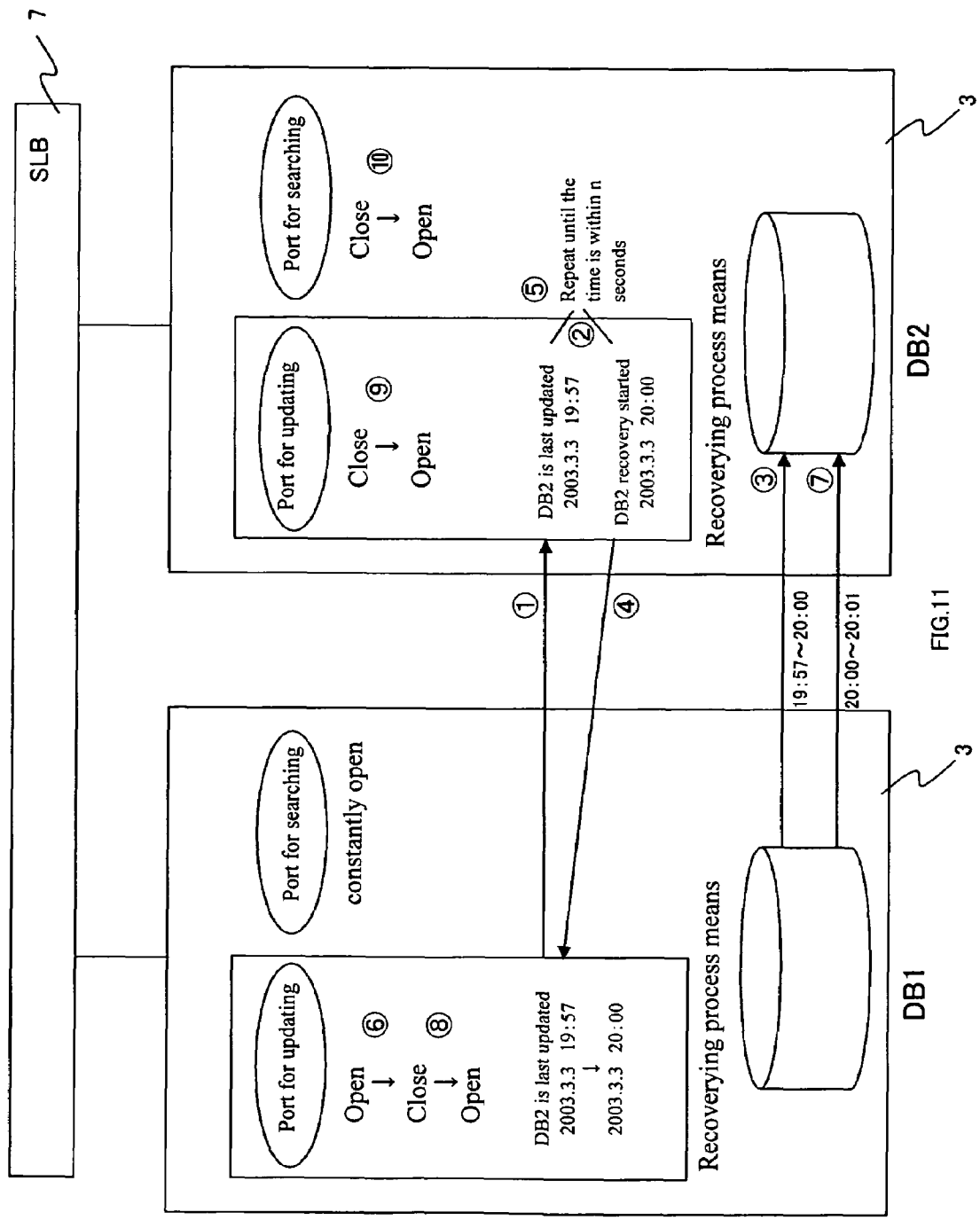
FIG. 11 is an illustration of a data recovery process by the image database server.
Figure 12:
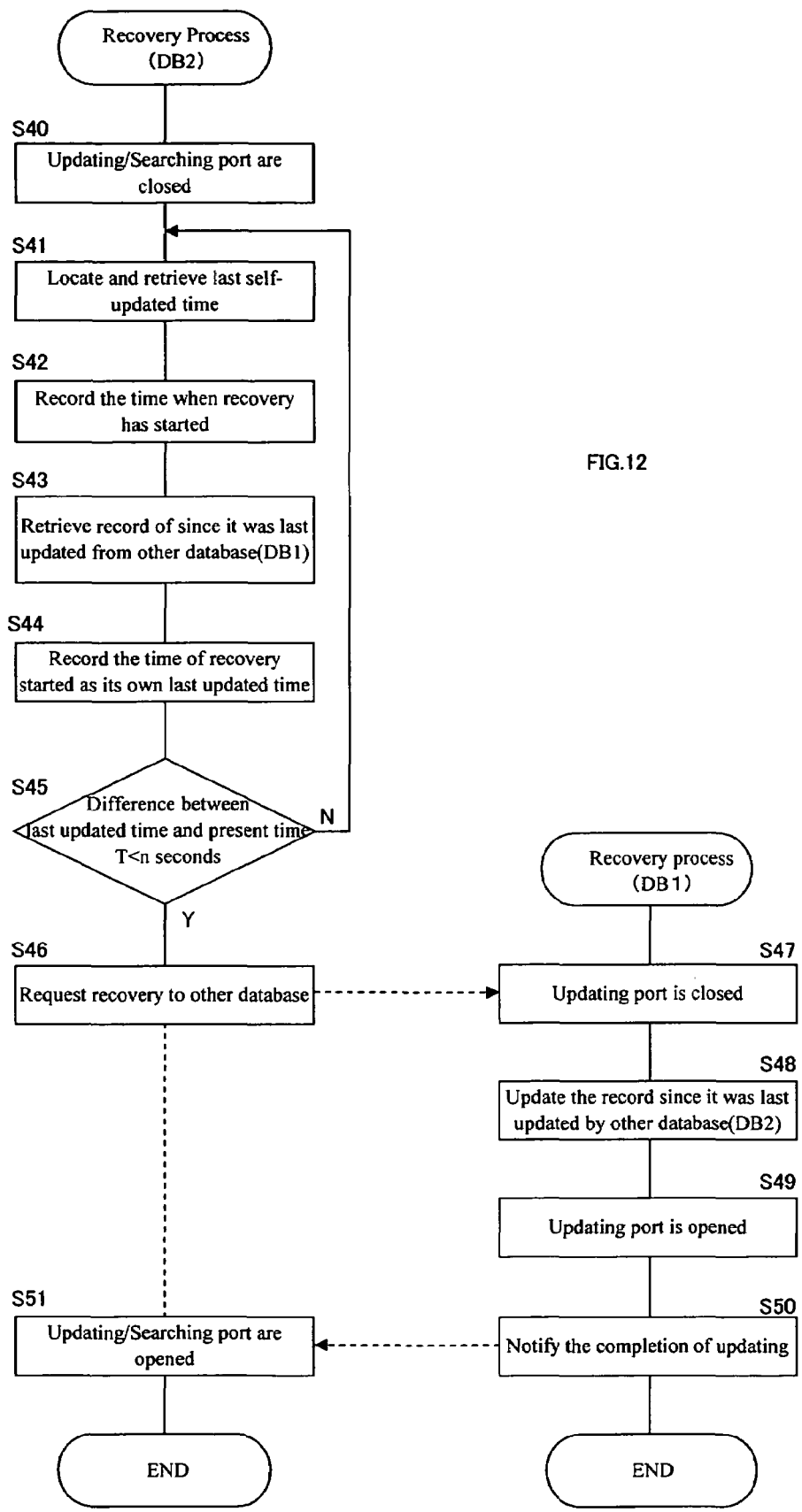
FIG. 12 is a flow chart showing the data recovery process by the image database server.

At the time of the restoration from the above failure state, one of the image database servers 3 performs normal operation, and the both ports of the other image database server 3 are closed. As shown in FIGS. 11 and 12, the other image database server 3 returning from failure retrieves the last self updated time from one of the image database servers 3 (step 1 shown in FIG. 11), and records restoration start time (step 2 shown in FIG. 11). Next, the record of the updated time after retrieving at the first step is retrieved from one of the image database servers 3, and the own database is updated (step 3 shown in FIG. 11). The restoration start time recorded at the step 2 is set to the last updated time of own database (step 4 shown in FIG. 11), the last updated time of the step 4 is compared with the present time. The above steps are repeated until the time is within n seconds. Herein, n is several seconds. If the time is within n seconds, the recovering operation will be requested to one of the image database servers 3 (step 5 shown in FIG. 11). On the other hand, one of the image database servers 3 closes the port for updating data, and updates the database after the time of the last update of the other image database server 3 (step 6 shown in FIG. 11) (step 7 shown in FIG. 11). The image database server 3 opens the port for updating after completing the update processing (step 8 shown in FIG. 11), and transfers the notice of termination to the other image database server 3. The other image database server 3 opens both the ports, and returns to the normal operation (steps 9, 10 shown in FIG. 11). Though both the port for updating and the port for retrieving are separately constituted in the above explanation, it is also possible to constitute the port for updating and the port for retrieving as the same port.

Another embodiment will be explained below. The above embodiment explains the system in which the high order layers of the session layer or more are operated by the DICOM protocol which is the image diagnostic standard in the medical field or the other local protocol. However, terminals such as the viewer may correspond to WEB. In this case, for example, a WEB server group containing a plurality of WEB servers is provided in the basic frame described above, and is operated under the control of the load balancer 7.

In the above system, any one of or all of the storage unit, the control unit, the image database server 3 and the DICOM gateway is hot-swappable in the unit, and thereby the system can be maintained while the operating state of the system is maintained.

Though the above embodiments explain the system in which the control unit is provided with the operating state inspection means for inspecting the operating state of the storage unit, the control unit may be further provided with the operating state inspection means for the server group such as the load balancer, the image database server and the DICOM gateway as network equipment. Specifically, the control unit accesses the load balancer and each server group in order through the second network N2, and inspects the operating states. The control unit updates and stores the result in the table showing the operating state of the image database server. The load balancer and each server monitor obstacles generated during transmission and reception of data with any other server through the first network N1, and store these histories in their operating state data storage areas. When the control unit accesses, the operating state can be grasped by reading the history data. Herein, the operating state inspection means to the server group such as the load balancer, the image database server and the DICOM gateway can be constructed not only in the control unit, but also in any server such as the image database server and the DICOM gateway.

The system is provided with monitor display means for displaying the operating state data, and the operating state data is displayed and controlled by the image database server or the control unit. Thereby, the operating state of the system can be grasped by an administrator, and a suitable maintenance can be performed. Further, for example, a mail server is constructed in the load balancer, and thereby the operating state data stored in the database server can be mail-transmitted to the administrator. In this case, the control efficiency of the system due to the administrator can be greatly enhanced by transferring the contents to the administrator at the time of the generation of the obstacle, and at the changing timing of system operating states such as the start and completion of the recovery process caused by the generation of the obstacle.

Thus, since the exchange processing or the like of the obstacle generating part can be performed without stopping the system by multiplexing the system, and the exchanged part is automatically restored, the reliability of the system can be greatly enhanced.

As described above, the present invention can provide the highly reliable image database system capable of accessing the image data at high speed to the apparatus using the DICOM protocol regardless of the increase of the image data, and capable of controlling the image data as a whole.

As described above, though the suitable embodiments of the present invention are explained, the present invention is not limited thereto. Variations may be made as required without departing from the technical concept of the present invention.

What is claimed is:

1. An image database system comprising:
   a plurality of storage units for storing medical image data;
   a plurality of control units for controlling the storage units;
   a plurality of image database servers storing attribute information including key information associated with the medical image data stored in the storage units therein and for applying relay processing of the medical image data between an externally connected apparatus and the image database servers;
   a first network connected to the storage units, control units and image database servers for connecting each other through a first switch for processing a job related to an external request, and
   a second network connected to the storage units, control units and image database servers for connecting each other through a second switch for processing a job related to an internal request, wherein each of the image database servers includes:

a port for updating data and a port for retrieving data for the first network;

an updating portion for updating a database of a corresponding image database server by writing in an updated time on a record for update processing of data performed through the first network and for updating a database of another image database server by writing in the updated time on a record through the second network; and a recovery process portion for opening the ports for updating data and the ports for retrieving data of both of an image database server that returns from failure and an image database server that is normally operated, the recovery process portion opening the ports 1) when the image database server that returns from failure closes the port for updating data and the port for retrieving data to the first network, updates the database by retrieving a record between a time of a last update before the failure and a restoration start time from the image database server that is normally operated through the second network, and repeats update processing of setting the restoration start time as the last updated time until time difference between the last updated time and a present time is within a predetermined time, and 2) when the image database server that is normally operated closes the port for updating data to the first network upon the time difference being within the predetermined time and performs update processing of writing in on the record of the database of the image database server that returns from failure, the record of the database of the image database server that is normally operated after the last updated time of the image database server that returns from failure through the second network.

2. A method for storing medical image data using an image database system comprising the steps of:

connecting a plurality of storage units, a plurality of control units and a plurality of image database servers to each other by a first network through a first switch for processing a job related to an external request;

controlling the storage units by the control units;

applying relay processing of the medical image data to the control units by the image database servers on the basis of an external request for storing the medical image data inputted from an externally connected apparatus in the storage units through a port for updating data to the first network;

storing attribute information that includes key information associated with the medical image data stored in the storage units by the image database servers therein;

connecting the storage units, the control units and the image database servers to each other by a second network through a second switch for processing a job related to an internal request;

updating a database of a corresponding image database server therein by writing in an updated time on a record for update processing of data performed through the first network and for updating a database of another image database server therein by writing in the updated time on a record through the second network;

retrieving the medical image data stored in the storage units by the image database server on the basis of the external request from the externally connected apparatus through a port for retrieving data to the first network;

a first recovery process for a first image database server that returns from failure, comprising the steps of:

closing the port for updating data and the port for retrieving data to the first network;

updating the database by retrieving a record between a time of a last update before the failure and a restoration start time from at least one of the image database servers that is normally operated through the second network; and repeating update processing of setting the restoration start time as the last updated time until time difference between the last updated time and a present time is within a predetermined time;

a second recovery process for the image database server that is normally operated, comprising the steps of:

closing the port for updating data to the first network upon the time difference being within the predetermined time; and performing update processing of writing in the record of the database of the first image database server that returns from failure the record of the database of the image database server that is normally operated after the last updated time of the first image database server that returns from failure through the second network; and opening the ports for updating data and the ports for retrieving data of the first image database server that returns from failure and the other image database servers that are normally operated, upon completion of the first and second recovery processes.

* * * * *